US009687171B2

(12) United States Patent
Kitane

(10) Patent No.: US 9,687,171 B2
(45) Date of Patent: Jun. 27, 2017

(54) MAGNETIC RESONANCE IMAGING APPARATUS AND MAGNETIC RESONANCE IMAGING METHOD

(75) Inventor: Shinichi Kitane, Nasushiobara (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 843 days.

(21) Appl. No.: 12/538,957

(22) Filed: Aug. 11, 2009

(65) Prior Publication Data

US 2010/0041982 A1    Feb. 18, 2010

(30) Foreign Application Priority Data

Aug. 12, 2008  (JP) .................................. 2008-208181
Jun. 4, 2009   (JP) .................................. 2009-135298

(51) Int. Cl.
| | |
|---|---|
| *A61B 5/05* | (2006.01) |
| *A61B 5/055* | (2006.01) |
| *A61B 5/00* | (2006.01) |
| *G01R 33/563* | (2006.01) |
| *A61B 5/026* | (2006.01) |
| *G01R 33/3415* | (2006.01) |
| *G01R 33/567* | (2006.01) |

(52) U.S. Cl.
CPC ............ *A61B 5/055* (2013.01); *A61B 5/0037* (2013.01); *A61B 5/0263* (2013.01); *A61B 5/7285* (2013.01); *G01R 33/5676* (2013.01); *G01R 33/56316* (2013.01); *A61B 5/026* (2013.01); *G01R 33/3415* (2013.01); *G01R 33/5673* (2013.01)

(58) Field of Classification Search
CPC  A61B 8/00; G01R 33/5673; G01R 33/56318; G01R 33/56391; G01R 33/5613; G01R 33/5614; G01R 33/5615
USPC ....... 600/301, 407, 410, 413, 419, 428, 437, 600/448, 454, 455, 456, 458, 468; 324/306, 307, 309, 313
See application file for complete search history.

(56) References Cited

U.S. PATENT DOCUMENTS

| | | | | |
|---|---|---|---|---|
| 5,560,360 | A * | 10/1996 | Filler et al. ................... | 600/408 |
| 6,507,190 | B1 * | 1/2003 | Hinks et al. ................... | 324/307 |
| 2003/0083569 | A1 * | 5/2003 | Edelman ........................ | 600/410 |
| 2003/0225328 | A1 * | 12/2003 | DeMeester et al. .......... | 600/419 |
| 2005/0007112 | A1 * | 1/2005 | Deimling ...................... | 324/307 |
| 2005/0033154 | A1 * | 2/2005 | deCharms ..................... | 600/410 |
| 2005/0272995 | A1 * | 12/2005 | Prince .......................... | 600/407 |
| 2006/0025688 | A1 * | 2/2006 | Hayase et al. ................ | 600/454 |
| 2006/0241402 | A1 * | 10/2006 | Ichihara et al. .............. | 600/425 |
| 2006/0253015 | A1 * | 11/2006 | Nezafat et al. ............... | 600/410 |
| 2006/0293586 | A1 * | 12/2006 | Hillenbrand et al. ........ | 600/410 |
| 2007/0078333 | A1 * | 4/2007 | Abe et al. ..................... | 600/420 |

(Continued)

*Primary Examiner* — Amanda Lauritzen Moher
(74) *Attorney, Agent, or Firm* — Nixon & Vanderhye P.C.

(57) ABSTRACT

A magnetic resonance imaging apparatus includes a trigger generating unit, a blood flow image generating unit and a control unit. The trigger generating unit acquires blood flow information of an object and generates a trigger based on the blood flow information. The blood flow image generating unit acquires imaging data with using the trigger and generates blood flow image data. The control unit controls so as to repeatedly perform a probe sequence for acquiring the blood flow information and an imaging sequence for acquiring the imaging data alternately.

17 Claims, 10 Drawing Sheets

(56) References Cited

U.S. PATENT DOCUMENTS

2007/0083105 A1\* 4/2007 Miyazaki et al. ............ 600/410
2007/0285094 A1\* 12/2007 Reeder et al. ................ 324/313
2008/0081987 A1\* 4/2008 Miyazaki ............... A61B 5/055
   600/410

\* cited by examiner

MAGNETIC RESONANCE IMAGING APPARATUS AND MAGNETIC RESONANCE IMAGING METHOD

BACKGROUND OF THE INVENTION

1. Technical Field

The present exemplary embodiments relate to a MRI (magnetic resonance imaging) apparatus and a magnetic resonance imaging method which excite nuclear spin of an object magnetically with a RF (radio frequency) signal having the Larmor frequency and reconstruct an image based on NMR (nuclear magnetic resonance) signals generated due to the excitation, and more particularly, to a magnetic resonance imaging apparatus and a magnetic resonance imaging method which make it possible to perform MRA (magnetic resonance angiography) for obtaining a blood flow image with using blood flow information as a trigger.

2. Related Art

Magnetic Resonance Imaging is an imaging method which excites nuclear spins of an object set in a static magnetic field with an RF signal having the Larmor frequency and reconstructs an image based on NMR signals generated due to the excitation.

In the field of magnetic resonance imaging, as a method of obtaining an image of a blood flow, MRA is known. MRI that does not use a contrast medium is referred to as non-contrast MRA. As non-contrast MRA, an FBI (fresh blood imaging) method performs ECG (electro cardiogram) synchronization to capture a pumping blood flow ejected from the heart, thereby satisfactorily representing a blood vessel (for example, refer to JP-A No. 2000-5144). The FBI method is an imaging method for acquiring an angio image as a transverse relaxation (T2) weighted image by a three dimensional scan with a SE (spin echo) sequence.

Further, ECG-prep as a related technology used with the FBI method is devised to measure an appropriate delay time for ECG synchronization (see, for example, U.S. Pat. No. 6,144,201). ECG-prep is a technique that performs an ECG-prep scan as a preparation scan to decide upon an appropriate delay time for ECG synchronization for imaging an angio image satisfactorily prior to an FBI scan for diagnostic imaging and subsequently the FBI scan is performed with the ECG delay time decided upon by the ECG-prep scan. The ECG-prep scan is a pre-scan to obtain plural angio images at mutually different time phases by acquiring data while gradually changing delay times from a trigger R wave of an ECG. By selecting an angiogram, corresponding to a time phase at which brightness in a blood vessel part is higher, from the plural angiograms obtained by the ECG-prep scan, an ECG delay time for the FBI scan can be determined.

Meanwhile, a PC (phase contrast) MRA method is known as another method for non-contrast-enhanced MRA (see, for example, Japanese Publication of Patent Application No. 63-230157). The PC MRA method is also called a PS (phase shift) MRA method and an imaging method to generate an image of a blood flow from phase information of spins. More specifically, in the PC MRA method, only moving spins are imaged selectively using a phenomenon that phases of static spins do not change before and after application of a bipolar gradient magnetic field, in contrast, phases of moving spins in blood flow shift before and after application of the bipolar gradient magnetic field in case where the bipolar gradient magnetic field is applied. A gap in phase of spins generated after applying a gradient magnetic field depends on an intensity and an application period of the applied gradient magnetic field and a velocity of a spin. That is, a phase of a spin can be expressed as a function of an intensity and an application period of a gradient magnetic field and a velocity of spins. Therefore, a blood flow velocity and a direction of blood flow can be calculated from phase information of spins.

As another non-contrast-enhanced MRA technology, a TOF (time of flight) method is known. The TOF method is a method to apply a saturation pulse to a blood flow to be a target and to image saturated blood signals flowing into an imaging section using inflow effect. In the PC MRA method and the TOF method, a blood vessel image is obtained as a longitudinal relaxation (T1) weighted image with a sequence of FE (field echo) type.

However, in the conventional MRA with ECG synchronization synchronous, an appropriate delay time is determined by performing an ECG-prep scan or another method before performing an imaging scan. Therefore, in case where a state of an object when a delay time is determined is different from that in performing an imaging scan, an appropriate delay time may be also changed. When an appropriate delay time during an ECG-prep scan is different from that during an imaging scan, an imaging scan is performed with an inappropriate delay time determined by performing the ECG-prep scan. Consequently, there is a problem that data is acquired at inappropriate timings and a blood vessel image cannot be obtained with a steady image quality and contrast.

BRIEF SUMMARY

The present exemplary embodiments have been made in light of the conventional situations, and it is an object to provide a magnetic resonance imaging apparatus and a magnetic resonance imaging method which make it possible to acquire data at a timing suited to the state of an object during an imaging scan to obtain a blood vessel image more stably.

The present exemplary embodiments provide a magnetic resonance imaging apparatus comprising: a trigger generating unit configured to acquire blood flow information of an object by acquiring magnetic resonance signals from the object and generate a trigger based on the blood flow information; a blood flow image generating unit configured to acquire imaging data from the object with using the trigger and generate blood flow image data with using the imaging data; and a control unit configured to control so as to repeatedly perform a probe sequence for acquiring the blood flow information and an imaging sequence for acquiring the imaging data alternately, in an aspect to achieve the object.

The present exemplary embodiments also provide a magnetic resonance imaging method comprising: acquiring blood flow information of an object by acquiring magnetic resonance signals from the object and generating a trigger based on the blood flow information; acquiring imaging data from the object with using the trigger and generating blood flow image data with using the imaging data; and controlling so as to repeatedly perform a probe sequence for acquiring the blood flow information and an imaging sequence for acquiring the imaging data alternately, in an aspect to achieve the object.

The magnetic resonance imaging apparatus and the magnetic resonance imaging method according to the present exemplary embodiments as described above make it possible to acquire data at a timing suited for a state of an object during an imaging scan to obtain a blood vessel image more stably.

DESCRIPTION OF THE PREFERRED EMBODIMENTS

A magnetic resonance imaging apparatus and a magnetic resonance imaging method according to embodiments of the present invention will be described with reference to the accompanying drawings.
(Configuration and Function)

Figure 1:
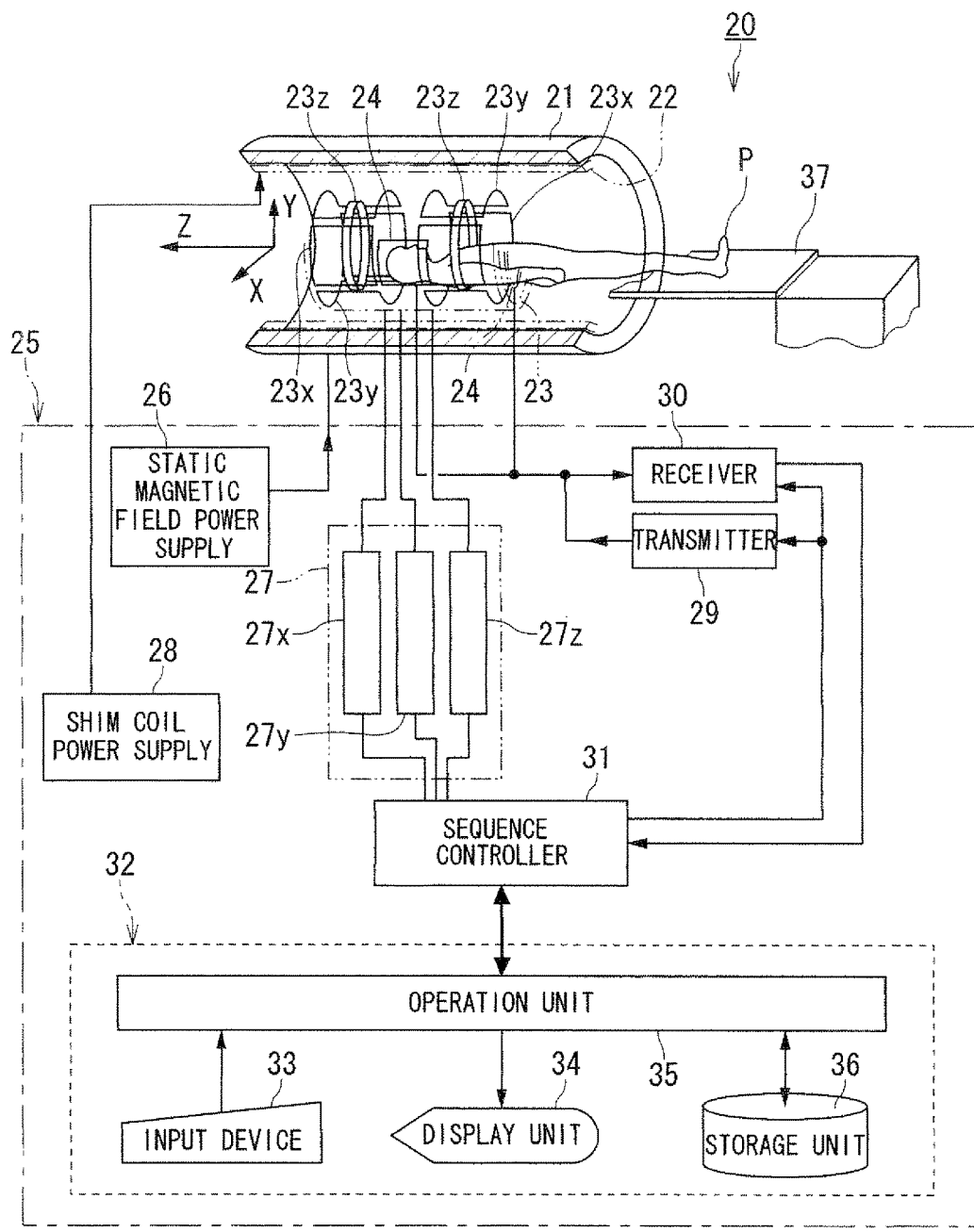
FIG. 1 is a block diagram showing a magnetic resonance imaging apparatus according to an embodiment of the present invention.

FIG. 1 is a block diagram showing a magnetic resonance imaging apparatus according to an embodiment of the present invention.

A magnetic resonance imaging apparatus 20 includes a static field magnet 21 for generating a static magnetic field, a shim coil 22 arranged inside the static field magnet 21 which is cylinder-shaped, a gradient coil 23 and RE coils 24.

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27x, a Y-axis gradient power supply 27y and a Z-axis gradient power supply 27z. The computer 32 includes an input device 33, a display unit 34, a operation unit 35 and a storage unit 36.

The static field magnet 21 communicates with the static magnetic field power supply 26. The static magnetic field power supply 26 supplies electric current to the static field magnet 21 to get the function to generate a static magnetic field in a imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil 23 includes an X-axis gradient coil 23x, a Y-axis gradient coil 23y and a Z-axis gradient coil 23z. Each of the X-axis gradient coil 23x, the Y-axis gradient coil 23y and the Z-axis gradient coil 23z which is cylinder-shaped is arranged inside the static field magnet 21. The gradient coil 23 has also a bed 37 in the area formed inside it which is an imaging area. The bed 37 supports an object P. The RF coils 24 include a whole body coil (WBC: whole body coil), which is built in the gantry, for transmission and reception of RE signals and local coils, which are arranged around the bed 37 or the object P, for reception of RE signals.

The gradient coil 23 communicates with the gradient power supply 27. The X-axis gradient coil 23x, the Y-axis gradient coil 23y and the Z-axis gradient coil 23z of the gradient coil 23 communicate with the X-axis gradient power supply 27x, the Y-axis gradient power supply 27y and the Z-axis gradient power supply 27z of the gradient power supply 27 respectively.

The X-axis gradient power supply 27x, the Y-axis gradient power supply 27y and the Z-axis gradient power supply 27z supply currents to the X-axis gradient coil 23x, the Y-axis gradient coil 23y and the Z-axis gradient coil 23z respectively so as to generate gradient magnetic fields Gx, Gy and Gz in the X, Y and Z directions in the imaging area.

The RF coils 24 communicate with the transmitter 29 and/or the receiver 30. The transmission RF coil 24 has a function to transmit a RF signal given from the transmitter 29 to the object P. The reception RF coil 24 has a function to receive a MR signal generated due to an nuclear spin inside the object P which is excited by the RF signal to give to the receiver 30.

Figure 2:
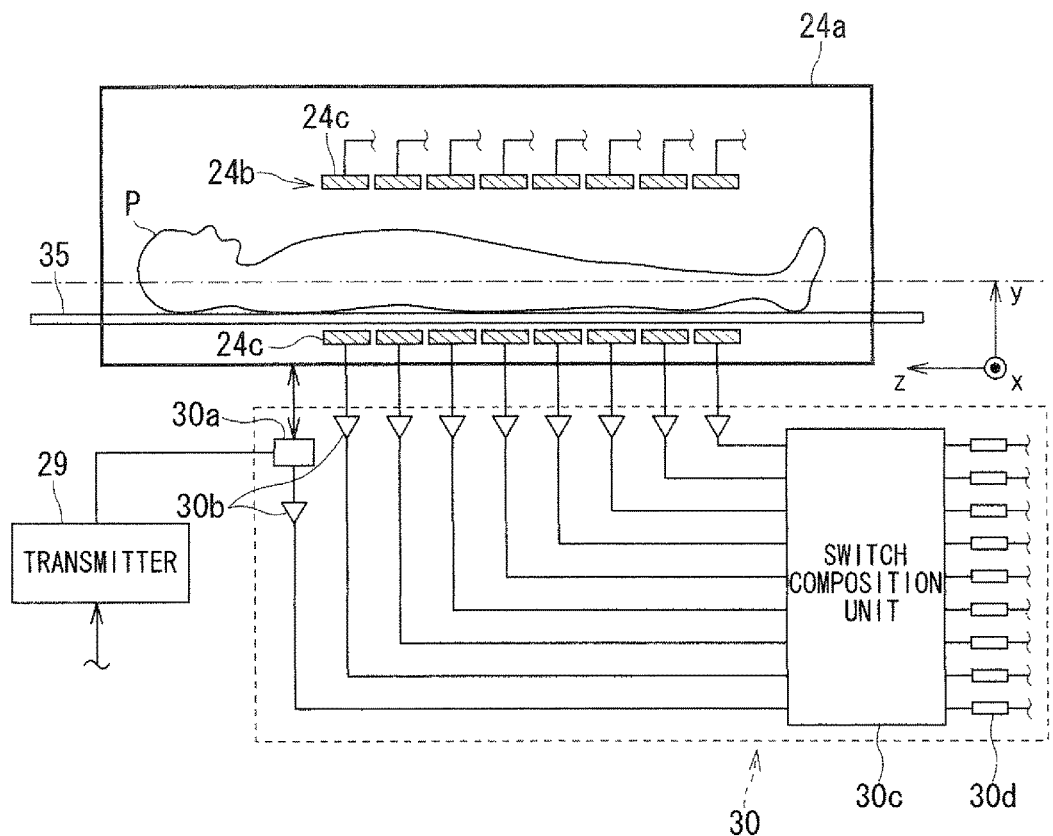
FIG. 2 is a diagram showing an example of detail structure of the RF coils shown in FIG. 1.
Figure 3:
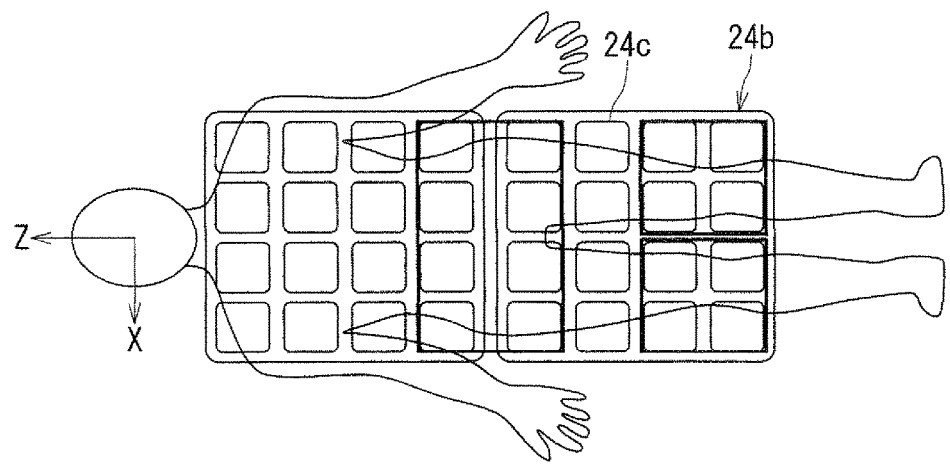
FIG. 3 is a diagram showing an example arrangement of the coil elements set on the body surface side of the object shown in FIG. 2.
Figure 4:
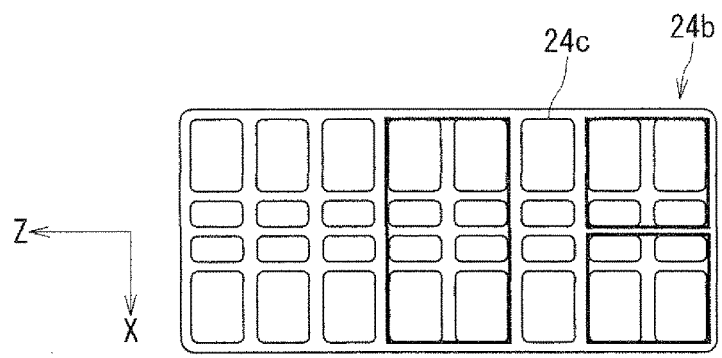
FIG. 4 is a diagram showing an example arrangement of the coil elements set on the back surface side of the object shown in FIG. 2.

FIG. 2 is a diagram showing an example of detail structure of the RE coils 24 shown in FIG. 1. FIG. 3 is a diagram showing an example arrangement of the coil elements 24c set on the body surface side of the object P shown in FIG. 2. FIG. 4 is a diagram showing an example arrangement of the coil elements 24c set on the back surface side of the object P shown in FIG. 2.

As shown in FIG. 2, the RF coils 24 include a cylindrical WB (whole-body) coil 24a, and a phased array coil 24b. The phased array coil 24b includes a plurality of coil elements 24c, and a plurality of the coil elements 24c is arranged on each of the body surface side and the back surface side of the object P.

For example, as shown in FIG. 3, on the body surface side of the object P, four rows of coil elements 24c are provided in the x-direction and eight columns of them in the z-direction, that is, a total of thirty two coil elements 24c are arranged so as to cover a wide-ranging imaging area. Likewise, as shown in FIG. 4, on the back surface side of the object, four rows of coil elements 24c are provided in the x-direction and eight columns of them in the z-direction, that is, a total of thirty two coil elements 24c are arranged so as to cover a wide-ranging imaging area. On the back surface side, surface coils 24 with a smaller size than that of the other coil elements 24c are arranged in the vicinity of the body axis from the viewpoint of sensitivity improvement, considering for the presence of the backbone of the object P.

On the other hand, the receiver 30 includes a duplexer 30a, amplifiers 30b, a switch composition unit 30c, and reception circuits 30d. The duplexer 30a is connected to the transmitter 29, the WB coil 24a, and the amplifier 30b for the WB coil 24a. The amplifiers 30b are provided by the total number of the coil elements 24c and the WB coil 24a, and each connected to a respective one of the coil elements 24c and the WE coil 24a. The switch composition unit 30c consists of a single piece or a plurality of pieces. The input side of the switch composition unit 30c is connected to the plurality of coil elements 24c or the WE coil 24a through the plurality of amplifiers 30b. The reception circuits 30d are provided by a desired number such as to be smaller than or equal to the total number of the coil elements 24c and the WB coil 24a, and disposed on the output side of the switch composition unit 30c.

The WB coil 24a can be used as a coil for the transmission of RE signals. As a coil for the reception of NMR signals, each of the coil elements 24c can be used. Furthermore, the WB coil 24a can also be used for a receiving coil.

Therefore, the duplexer 30a is configured so as to provide the WB coil 24a with RF signals for transmission, outputted from the transmitter 29, while providing the switch composition unit 30c with NMR signals received in the WE coil 24a via the amplifiers 30b in the receiver 30. An NMR signal received in each of the coil elements 24c is outputted to the switch composition unit 30c via a respective one of the amplifiers 30b.

The switch composition unit 30c is configured so as to perform composition processing and switching with respect to NMR signals received from the coil elements 24c or the WB coil 24a and to output them to the corresponding reception circuits 30d. In other words, the switch composition unit 30c is configured so that, in conformance with the number of the reception circuits 30d, the composition processing and switching with respect to NMR signals received from the coil elements 24c or the WB coil 24a are performed in the switch composition unit 30c, and that NMR signals can be received from various imaging areas by forming sensibility distributions in response to the imaging areas, using a plurality of desired coil elements 24c.

However, NMR signals may be received by WB coil 24a alone without providing the coil elements 24c. Also, NMR signals received in the coil elements 24c or the WB coil 24a may be directly outputted to the reception circuits 30d without providing the switch composition unit 30c. Furthermore, more coil elements 24c may be extensively arranged.

The sequence controller 31 of the control system 25 communicates with the gradient power supply 27, the transmitter 29 and the receiver 30. The sequence controller 31 has a function to storage sequence information describing control information needed in order to make the gradient power supply 27, the transmitter 29 and the receiver 30 drive and generate gradient magnetic fields Gx, Gy and Gz in the X, Y and Z directions and a RF signal by driving the gradient power supply 27, the transmitter 29 and the receiver 30 according to a predetermined sequence stored. The control information above-described includes motion control information, such as intensity, impression period and impression timing of the pulse electric current which should be impressed to the gradient power supply 27

The sequence controller 31 is also configured to give raw data to the computer 32. The raw data is complex data obtained through the detection of a NMR signal and A/D (analog to digital) conversion to the NMR signal detected in the receiver 30.

The transmitter 29 has a function to give a RF signal to the RE coil 24 in accordance with control information provided from the sequence controller 31. The receiver 30 has a function to generate raw data which is digitized complex number data by detecting a NMR signal given from the RE coil 24 and performing predetermined signal processing and A/D converting to the NMR signal detected. The receiver 30 also has a function to give the generated raw data to the sequence controller 31.

The computer 32 gets various functions by the operation unit 35 executing some programs stored in the storage unit 36 of the computer 32. Alternatively, some specific circuits having various functions may be provided with the magnetic resonance imaging apparatus 20 instead of using some of the programs.

Figure 5:
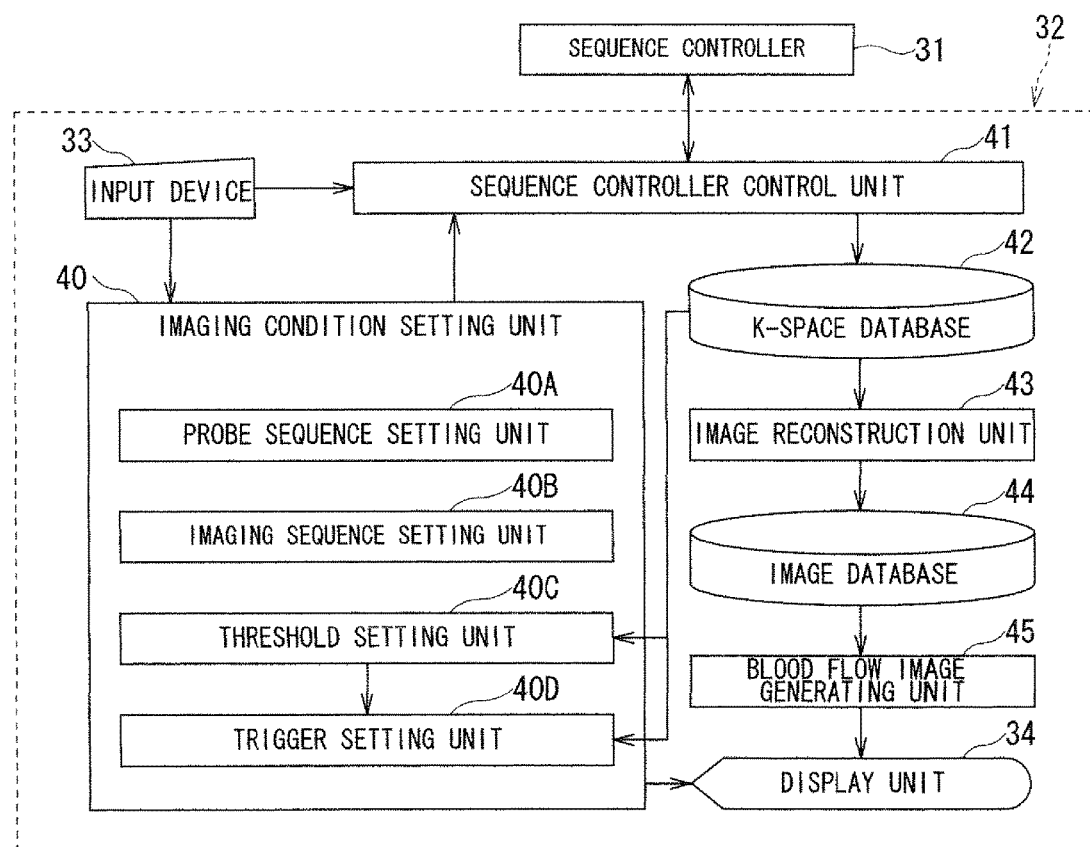
FIG. 5 is a functional block diagram of the computer shown in FIG. 1.

FIG. 5 is a functional block diagram of the computer 32 shown in FIG. 1.

The computer 32 functions as an imaging condition setting unit 40, a sequence controller control unit 41, a k-space database 42, an image reconstruction unit 43, an image database 44 and a blood flow image generating unit 45 by program. The imaging condition setting unit 40 includes a probe sequence setting unit 40A, an imaging sequence setting unit 40B, a threshold setting unit 40C and a trigger setting unit 40D.

The imaging condition setting unit 40 has a function to set an imaging condition including a pulse sequence based on information from the input device 33 displaying a screen for setting an imaging condition on the display unit 34 and to provide the set imaging condition to the sequence controller control unit 41. Especially, the imaging condition setting unit 40 has functions to set an imaging sequence for acquisition of imaging data for generating a blood flow image and a probe sequence for acquiring blood flow information referred for generating a trigger in an imaging sequence, to set a probe sequence as a pulse sequence for a pre-scan and set thresholds to a signal value of data, a phase shift amount of a blood flow signal or a blood flow velocity based on blood flow information obtained by a pre-scan, to set a pulse sequence in which single or plural probe sequences and an imaging sequence are repeated alternately as a sequence for an imaging scan, to determine whether a value of data acquired by the probe sequence is within a range specified by thresholds or not and to generate a trigger for performing an imaging sequence when the value of data is determined to be within the thresholds.

A function to set a probe sequence, a function to set an imaging sequence, a function to set thresholds to a signal value of data, a phase shift amount of a blood flow signal or a blood flow velocity and a function to perform threshold determination to set a trigger are provided with the probe sequence setting unit 40A, the imaging sequence setting unit 40B, the threshold setting unit 40C and the trigger setting unit 40D respectively. In the case where a trigger has generated, the imaging condition setting unit 40 is configured to output a predetermined pulse sequence to the sequence controller control unit 41.

Figure 6:
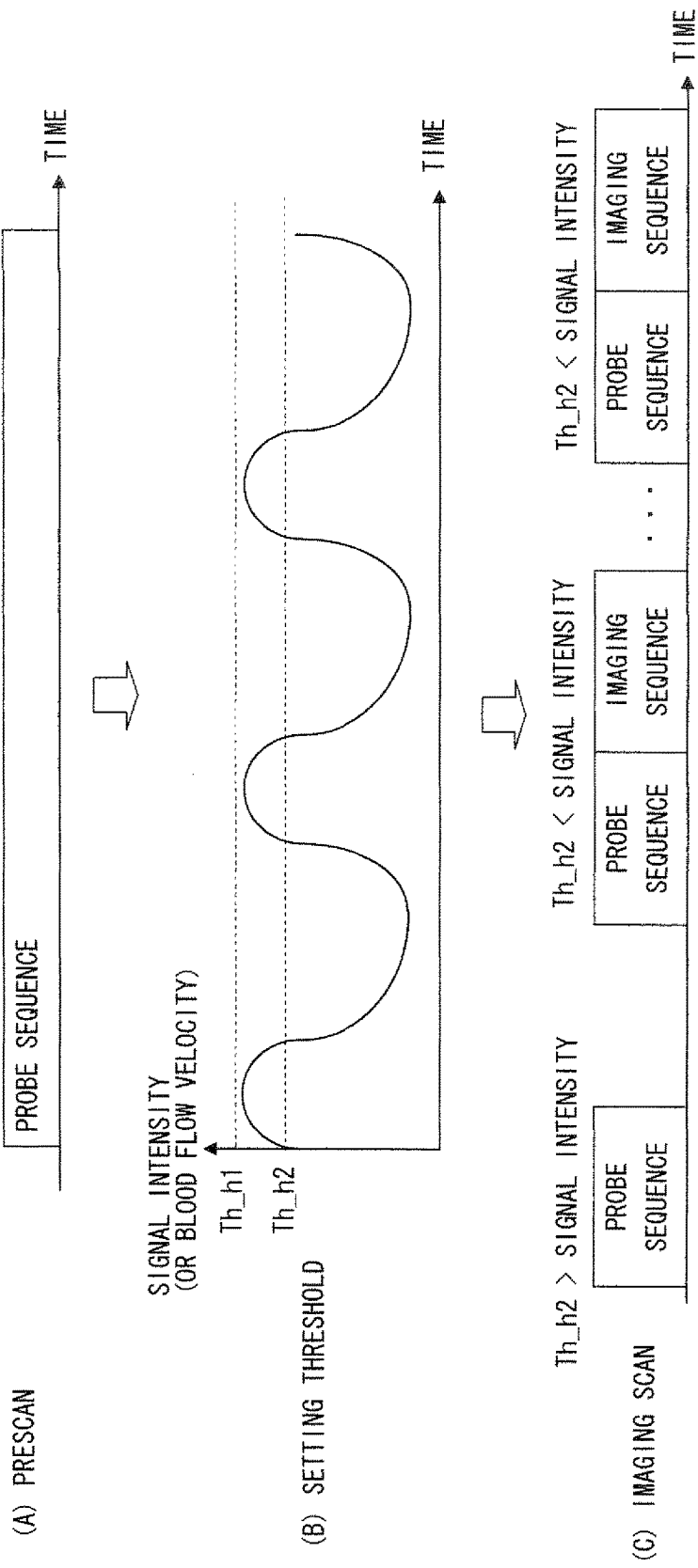
FIG. 6 is a diagram showing a procedure for performing a pre-scan and an imaging scan according to a probe sequence and an imaging sequence set in the imaging condition setting unit shown in FIG. 5.

FIG. 6 is a diagram showing a procedure for performing a pre-scan and an imaging scan according to a probe sequence and an imaging sequence set in the imaging condition setting unit 40 shown in FIG. 5.

In FIGS. 6, (A), (B) and (C) respectively show a pre-scan with a probe sequence, an example of setting thresholds based on blood flow information acquired by the pre scan and an imaging scan in which the probe sequence and the imaging sequence are repeated alternately. Each abscissa axis of (A), (B) and (C) in FIG. 6 denotes time, and the ordinate axis of (B) in FIG. 6 denotes intensity of blood flow signal or velocity of blood flow. Note that, the ordinate axis of (B) in FIG. 6 may denote phase shift amount of blood flow signal.

As shown in FIG. 6 (A), a probe sequence for a pre-scan is set by the probe sequence setting unit 40A. An arbitrary sequence can be used as a probe sequence as long as the sequence can obtain a change of signals from a target vessel, a temporal phase change in signals from a target vessel or a velocity change of blood flow that flows in a target vessel as blood flow information. That is, the probe sequence is set to be a sequence for acquiring blood flow information such as a peak value of raw data from a target vessel, a peak value of absolute values of raw data from a target vessel, a peak value of brightness values in image data generated from raw data from a target vessel, a temporal phase change in a signal from a blood flow that flows in a target vessel or a velocity of a blood flow that flows in a target vessel.

For example, when a peak value of raw data from a target vessel, a peak value of absolute values of raw data from a target vessel or a peak value of brightness values in image data is obtained as blood flow information, a section region or a three-dimensional region including the target vessel is excited locally like a pencil excitation and a FE type or SE type of sequence for dynamically acquiring k-space data (k0 data) corresponding to a single line passing a center of k-space (also referred to Fourier space) from an entire slice or volume including the excited target vessel can be set as a probe sequence. In this case, setting a probe sequence of a same kind as that of an imaging sequence makes setting an imaging condition easy.

Meanwhile, when a velocity of a blood flow that flows in a target vessel is obtained as blood flow information, a flow sequence may be set to a probe sequence. When k-space data (k0 data) corresponding to a single line passing a center of k-space is acquired with a flow sequence, a velocity of a blood flow can be obtained. Specifically, when two pieces of raw data are acquired by controlling a gradient magnetic field by using a velocity encoding (VENC) gradient magnetic field having a gradient intensity according to velocities in two axis directions or a flow sequence with a flow pulse for producing a phase shift, a phase difference obtained by subtraction of the pieces of raw data and can be converted into a velocity having components in two axis directions. In this case, generally, imaging with VENC is performed twice but with respectively inverted polarities.

In the case of obtaining a temporal phase change in a signal from a blood flow that flows in a target vessel as blood flow information, the phase change in signal can be obtained using a PC sequence with application of a MPG (motion probing gradient) pulse having a single polarity. For example, a time variation in phase change amount of signal can be obtained by sequentially calculating a difference between a phase of a reference signal and a phase of a signal at each time phase. Alternatively, a time variation in phase change amount of a signal can be obtained also by sequentially calculating phase differences between temporal adjacent signals. Note that, if a difference between a phase of a reference signal and a phase of a signal in each time phase is calculated as a phase change amount of a signal, it is considered that blood flow information to which the characteristic of the change appears more satisfactory can be obtained.

When a peak value of raw data from a blood vessel, a peak value of absolute values of raw data from a blood vessel, a velocity of a blood flow or a phase shift amount in a signal obtained at each time by performing a probe sequence dynamically is plotted in the time axis direction, plot data as shown in FIG. 6 (B) can be obtained. For example, if raw data acquired by performing a probe sequence is subjected to FFT (fast Fourier transform), the absolute values of the raw data can be obtained. When the maximum value of the absolute values of the raw data is plotted, plot data showing a time change in intensity of a blood flow signal to be a target can be obtained. On the other hand, even if the peak value of the raw data is plotted as it is without performing FFT, similar plot data can be obtained.

As mentioned above, plot data showing a velocity of a blood flow in a target vessel, an intensity of a blood flow signal or a time variation in phase change amount can be obtained as probe data with maintained time resolution by performing bolus tracking using a probe sequence such as a PC sequence or a flow sequence. Note that, k-space data corresponding to a few lines near k0 data may be acquired with a probe sequence. However, the time resolution can be improved by reducing data to be acquired. Especially, if only k-space data for a single line is acquired with a probe sequence, the time resolution can be improved to the maximum.

Since probe data shows a signal intensity from a blood flow, a phase change amount of a signal or a time change of a velocity, the probe data changes in synchronization with a heart rate. Then, it can be thought that a period when a signal intensity from a blood flow becomes high enough, a period when a phase change amount of a signal becomes large enough or a period when a flow velocity of a blood flow is fast enough is a suitable period for acquisition of imaging data. That is, if a trigger is set as an imaging condition so that imaging data is acquired in a period when a signal intensity from a blood flow becomes high enough, a period when a phase change amount of a signal is large or a period when a flow velocity of a blood flow is fast enough, a signal from the blood flow can be consistently acquired with a satisfactory intensity.

For that purpose, thresholds to determine in an imaging scan whether a signal intensity from a blood flow or a phase change amount of a signal becomes large enough or whether a flow velocity of a blood flow becomes fast enough to generate a trigger signal are determined based on the probe data in the threshold setting unit 400. Determination of thresholds can be also performed automatically by detecting a period during which a signal intensity is relatively high based on signal values of the probe data in the threshold setting unit 40C for example. Alternatively, a user can set thresholds manually with operation of the input device 33 by displaying the probe data on the display unit 34.

In the example shown in FIG. 6 (B), a threshold Th_1 on the upper limit side and a threshold Th_2 on the lower limit side of a range determined that the signal intensity is relatively large are determined.

On the other hand, as shown in FIG. 6 (C), a sequence for an imaging scan is set in the imaging sequence setting unit 40B. As shown in FIG. 6 (B), when the thresholds to determine whether a timing is suitable for acquisition of imaging data have been determined, it becomes possible to perform the sequence for the imaging scan shown in FIG. 6 (C) by using the thresholds as one imaging condition.

As shown in FIG. 6 (C), the sequence for the imaging scan is a sequence in which a probe sequence is performed repeatedly at a constant interval and an imaging sequence is performed subsequently to the probe sequence according as the result of threshold determination based on data acquired in the probe sequence. Note that, the repeated probe sequence for the imaging scan is set to a sequence for performing non-dynamic data acquisition to acquire only data corresponding to a single line or several lines in k-space necessary for determination of the thresholds. That is, the probe sequence is set to a short sequence, of which data acquisition time is approximately 100 to 200 µs, for acquiring only necessary data so that a period for performing the imaging sequence is kept.

Then, the trigger setting unit 40D generates a trigger signal for starting acquiring to begin imaging data when an intensity of a blood flow signal, a phase change amount of a signal or a flow velocity of a blood flow becomes within a range defined by the thresholds. In the case of generating a trigger based on an intensity of a blood flow signal, the trigger setting unit 40D obtains the signal from the blood flow acquired by performing the probe sequence from the k-space database 42. When it is determined that the signal intensity is between the threshold Th_1 on the upper limit side and the threshold Th_2 on the lower limit side, the trigger setting unit 40D generates a trigger signal for starting acquisition of imaging data.

Consequently, as shown in FIG. 6 (C), when it is determined that the signal intensity from the blood flow obtained by performing the probe sequence is between the threshold Th_1 on the upper limit side and the threshold Th_2 on the lower limit side, an imaging sequence is performed subsequently to the probe sequence. On the other hand, when it is determined that the signal intensity from the blood flow is not between the threshold Th_1 on the upper limit side and the threshold Th_2 on the lower limit side, no imaging sequence is performed or an imaging sequence is performed without performing data acquisition till the following probe sequence. In the latter case, the sequence for the imaging scan becomes a sequence in which a probe sequence and an imaging sequence is repeated alternately like RMC (Real-time Motion Correction) that is a technology to correct a body motion of an object P in real time.

As mentioned above, thresholds for specifying a range in which an intensity of a signal from a blood flow becomes high enough can be determined prior to an imaging scan so that imaging data can be acquired only when an intensity of a signal from a blood flow is within the range specified with the thresholds in the imaging scan. Consequently, signals can be acquired with enough intensities to generate an angiogram stably.

When a trigger is generated based on a flow velocity of a blood flow or a phase change amount of a blood flow signal, the trigger setting unit 40D obtains a signal from a blood flow acquired by performing a flow sequence or a PC sequence as a probe sequence from the k-space database 42 and calculates the velocity of the blood flow or the phase change amount of the blood flow signal. When it is determined that the velocity of the blood flow or the phase change amount of the blood flow signal is between the threshold Th_1 on the upper limit side and the threshold Th_2 on the lower limit side, the trigger setting unit 40D generates a trigger signal for starting acquisition of imaging data.

As mentioned above, a velocity of a blood flow or a phase change amount of a blood flow signal can be monitored intermittently in an imaging scan with a flow sequence or a PC sequence as a probe sequence and a velocity range, corresponding to a flow velocity fast enough, in which it is considered that an inflow of a blood flow to an imaging region is large enough can be specified to generate a trigger to acquire imaging data. Consequently, it becomes possible to acquire imaging data at timings at which a sufficient amount of fresh blood flows into an imaging region constantly so that stable depicting of an angiogram can be performed.

Figure 7:
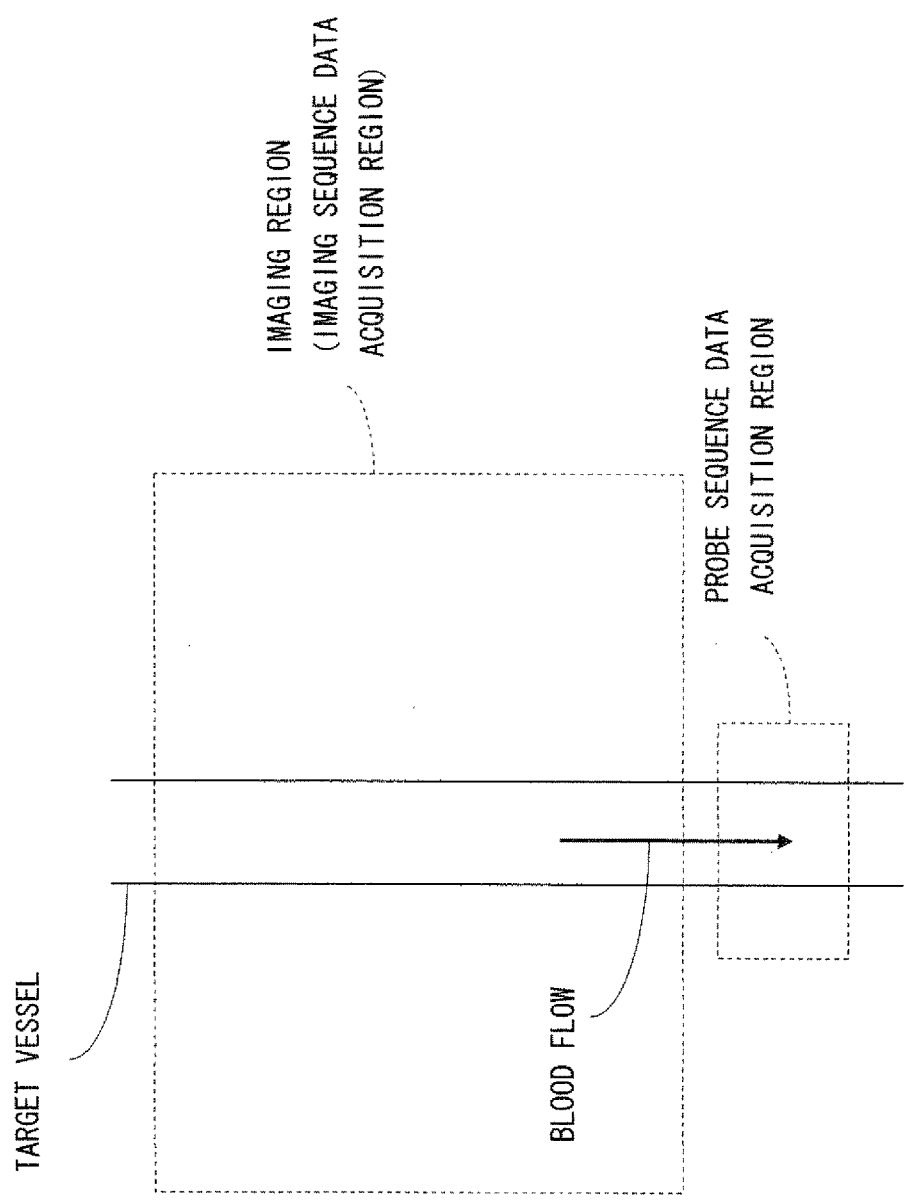
FIG. 7 is a diagram showing an example of respective data acquisition regions by the probe sequence and the imaging sequence shown in FIG. 6.

FIG. 7 is a diagram showing an example of respective data acquisition regions by the probe sequence and the imaging sequence shown in FIG. 6.

As shown in FIG. 7, a data acquisition region for an imaging sequence can be set arbitrarily as an imaging region for imaging a blood flow in a target vessel. On the other hand, a data acquisition region for a probe sequence can be set to a local region including at least the target vessel. Consequently, blood to be a target of blood flow information acquisition by the probe sequence can be a data acquisition target by the imaging sequence.

Note that, plural regions may be set as data acquisition regions with a probe sequence. In this case, appropriate thresholds can be set based on intensities of signals, phase change amounts of signals or flow velocities from or of blood flows flowing in plural regions. A data acquisition region by the probe sequence can be set inside or outside a data acquisition region by the imaging sequence. However, if the blood excited by performing the probe sequence is in a data acquisition region by the imaging sequence, signals from the blood excited by performing the probe sequence may affect imaging negatively. Therefore, as shown in FIG. 7, it is preferable that a data acquisition region by the probe sequence is set outside the data acquisition region by the imaging sequence, especially, to a sufficiently close position in the downstream side of the target vessel from the perspective of reducing signals unnecessary for imaging.

The imaging sequence can be set as an arbitrary sequence for imaging an angiogram. For example, an FE type sequence under a TOF method, a steady state free precession (SSFP) sequence, or a FSE (fast spin echo) sequence or a FASE (fast asymmetric spin echo or fast advanced spin echo) sequence with using half Fourier method under a FBI method can be set as an imaging sequence. That is, an appropriate sequence can be used as an imaging sequence according to an imaging condition such as a purpose of imaging and/or a range of excitation.

Note that, if the imaging sequence is set to a sequence for acquiring k-space data in the vicinity of the center in k-space first, the k-space data in the vicinity of the center in k-space can be acquired at timing nearer the acquisition timing of the probe data. Therefore, data in a low frequency region can be acquired at a more appropriate timing.

The SSFP sequence is a sequence for applying an RF excitation pulse at a same excitation angle (flip angle) in a constant and short repetition time (TR) to make a magnetization of spins a steady state, in which both the transverse magnetization and the longitudinal magnetization are not zero, for obtaining image data. Therefore, in the SSFP sequence, it becomes important to make the TR constant for maintaining a steady state of the spins. On the other hand, as shown in FIG. 6 (C), repeating the probe sequence and the imaging sequence at regular intervals alternately allows maintaining the steady state of the spins satisfactorily even in the case of using a SSFP sequence as an imaging sequence.

Similarly, when a FE sequence for which keeping a TR constant is important is used as an imaging sequence, repeating a probe sequence and an imaging sequence alternately at regular intervals allows a TR to be constant. In the case of imaging under the TOE method, imaging data is acquired at earlier data acquisition timing with a FE sequence and a T1 weighted image can be obtained as an angiogram.

In addition, PI (parallel imaging) as a high speed imaging technique may be used as a data acquisition method. PI is an imaging method for reducing the number of the phase encodes necessary for image reconstruction by receiving echo data with plural coil elements 24c and skipping phase encodes. In principle, the number of the phase encodes can be reduced down to the number derived by dividing the number of the phase encodes necessary for image reconstruction by the number of coil elements 24c. When PI is performed, information including the number of coil element 24c for acquiring echo data and information associating each coil element 24c with an imaging part necessary for PI is set as an imaging condition.

When a period of an imaging sequence is reduced by using PI together and a SSFP sequence or a FE sequence is used as an imaging sequence, a period of the imaging sequence can be made shorter enough than one period in a time variation of an signal intensity of a blood flow, a phase change amount of a blood flow signal or a blood flow velocity. Therefore, though data may not be acquired between adjacent probe sequences, the imaging data can be acquired every time a blood flow signal intensity, a phase change amount of a blood flow signal or a blood flow velocity is almost within a range defined by the thresholds. That is, it is considered that a case where a blood flow signal intensity, a phase change amount of a blood flow signal or a blood flow velocity becomes within a range defined by the thresholds once and subsequently changes outside the range defined by the thresholds is rare between probe sequences between which imaging data is not acquired.

Note that, plural ranges can be set by thresholds.

Figure 8:
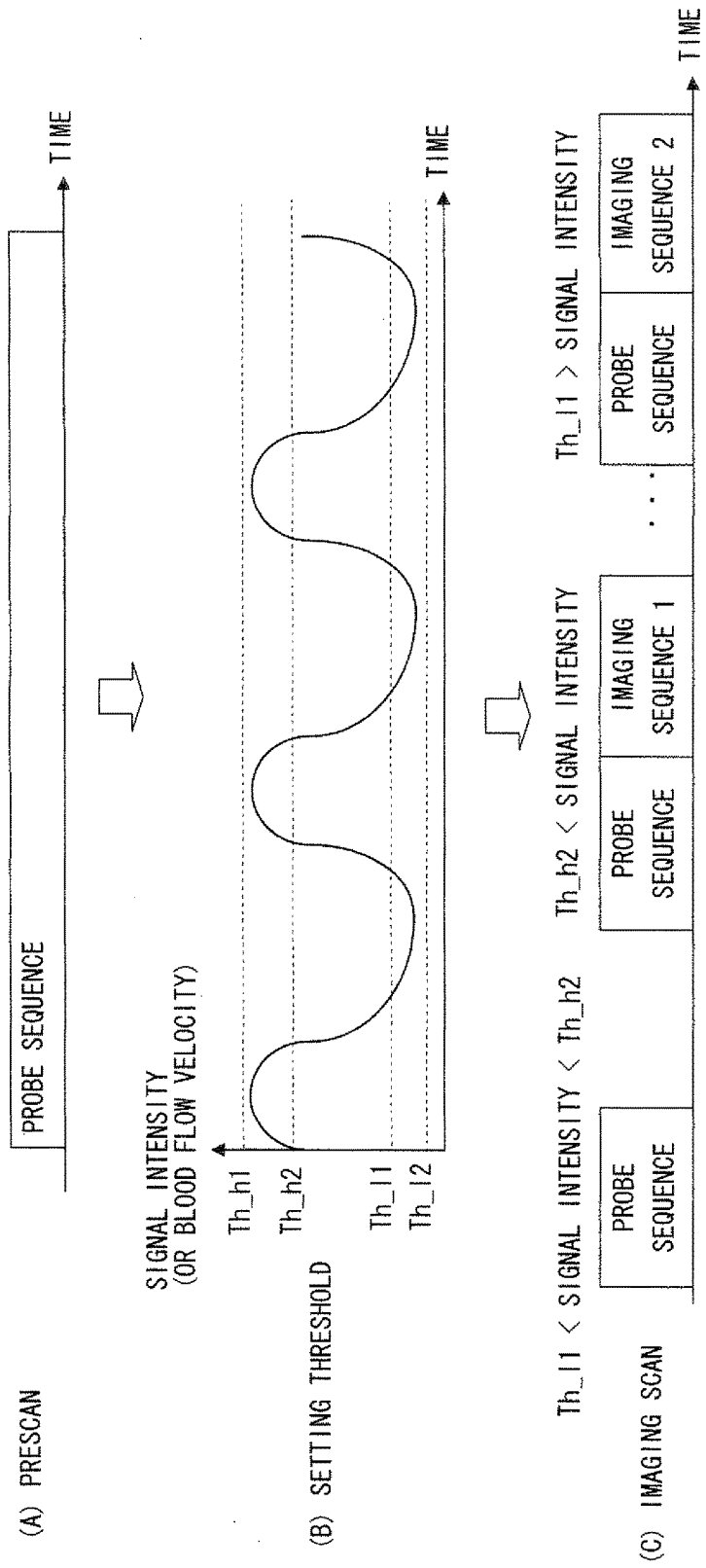
FIG. 8 is a diagram showing another example of procedure for performing a pre-scan and an imaging scan according to a probe sequence and an imaging sequence set in the imaging condition setting unit shown in FIG. 5.

FIG. 8 is a diagram showing another example of procedure for performing a pre-scan and an imaging scan according to a probe sequence and an imaging sequence set in the imaging condition setting unit 40 shown in FIG. 5.

In FIGS. 8, (A), (B) and (C) respectively show a pre-scan with a probe sequence, an example of setting thresholds based on blood flow information acquired by the pre scan and an imaging scan in which the probe sequence and the imaging sequence are repeated alternately. Each abscissa axis of (A), (B) and (C) in FIG. 8 denotes time, and the ordinate axis of (B) in FIG. 8 denotes intensity of blood flow signal or velocity of blood flow. Note that, the ordinate axis of (B) in FIG. 8 may denote phase shift amount of blood flow signal.

When the probe sequence set as shown in FIG. 8 (A) is performed, the probe data shown in FIG. 8 (B) is obtained. As shown in FIG. 8 (B), not only the threshold Th_h1 on the upper limit side and the threshold Th_h2 on the lower limit side to define a range in the vicinity of a local maximal value in the probe data but also the threshold Th_l1 on the upper limit side and the threshold Th_l2 on the lower limit side to define a range in the vicinity of a local minimal value can be set.

Thus, triggers can be generated so that imaging data is acquired also in a range where a signal intensity of a blood flow is low, a range where a phase change amount of a blood flow signal is small or a range where a blood flow velocity becomes a value close to zero, corresponding to the vicinity of a local minimal value of the probe data as well as in the vicinity of a local maximal value of the probe data.

Consequently, as shown in FIG. 8 (C), an imaging scan is performed. That is, when it is determined that an intensity of a signal from a blood flow, a phase change amount of a blood flow signal or a blood flow velocity acquired by performing a probe sequence is between the threshold Th_1 on the upper limit side and the threshold Th_2 on the lower limit side set to a local maximal value of the probe data, the first imaging sequence is performed subsequent to the probe sequence. When it is determined that an intensity of a signal from a blood flow, a phase change amount of a blood flow signal or a blood flow velocity acquired by performing a probe sequence is between the threshold Tl_1 on the upper limit side and the threshold Tl_2 on the lower limit side set to a local minimal value of the probe data, the second imaging sequence is performed subsequent to the probe sequence. On the other hand, when an intensity of a signal from a blood flow, a phase change amount of a blood flow signal or a blood flow velocity is not either between the threshold Th_1 on the upper limit side and the threshold Th_2 on the lower limit side corresponding to the local maximal value of the probe data or between the threshold Tl_1 on the upper limit side and the threshold Tl_2 on the lower limit side corresponding to the local minimal value of the probe data, an imaging sequence is not performed or an imaging sequence is performed without data acquisition till the following probe sequence.

The first imaging sequence is performed during a period in which an intensity of a blood flow signal, a phase change amount of a blood flow signal or a blood flow velocity is large. Therefore, image data in which a blood vessel is depicted can be obtained by reconstructing the image data from the k-space data acquired by performing the first imaging sequence. On the other hand, the second imaging sequence is performed during a period in which an intensity of a blood flow signal, a phase change amount of a blood flow signal or a blood flow velocity is small. Therefore, so-called BB (black blood) image data in which signals from a blood vessel are suppressed can be obtained by reconstructing the image data from the k-space data acquired by performing the second imaging sequence.

That is, by the imaging condition shown in FIG. 8, both image data depicting a blood vessel and image data depicting no blood vessel can be obtained. Additionally, if subtraction processing is performed between the image data depicting a blood vessel and the image data depicting no blood vessel, an angiogram in which an unnecessary blood vessel that is not an imaging target is not depicted and a target blood vessel is weighted selectively can be generated.

By the way, when imaging is performed with a FSE sequence or a FASE sequence as an imaging sequence under the FBI method, a TR of the imaging sequence may be over approximate one heart rate to plural heart rates even in case of using PI. In this case, the TR of the imaging sequence does not shorten enough to a period of the probe data that is assumed to correspond to a period of one heart rate. Therefore, especially, when a sequence with a long TR such as a FSE sequence or a FASE sequence is used as an imaging sequence and a probe sequence for acquiring k-space data for a single line and the imaging sequence are performed alternately, a case where a signal intensity of a blood flow, a phase change amount of a blood flow signal or a blood flow velocity becomes within a range defined by thresholds once and subsequently changes outside the range defined by the thresholds may increase between probe sequences between which no imaging data is acquired. That is, not only a period when no imaging data is acquired but also an imaging period may become long.

For that reason, in the case of using a sequence with a long TR as an imaging sequence, a probe sequence for acquiring k-space data corresponding to a single line or several lines may be repeated until a signal intensity of a blood flow, a phase change amount of a blood flow signal or a blood flow velocity acquired by performing a probe sequence becomes within a range defined by thresholds. That is, a time variation of a signal intensity of a blood flow, a phase change amount of a blood flow signal or a blood flow velocity can be monitored in real time during an imaging scan by dynamically performing probe sequences each acquiring k-space data corresponding to a single line or several lines and triggers can be generated so that an imaging sequence is started in each timing at which a predetermined signal intensity of a blood flow, a predetermined phase change amount of a blood flow signal or a predetermined blood flow velocity is acquired.

Figure 9:
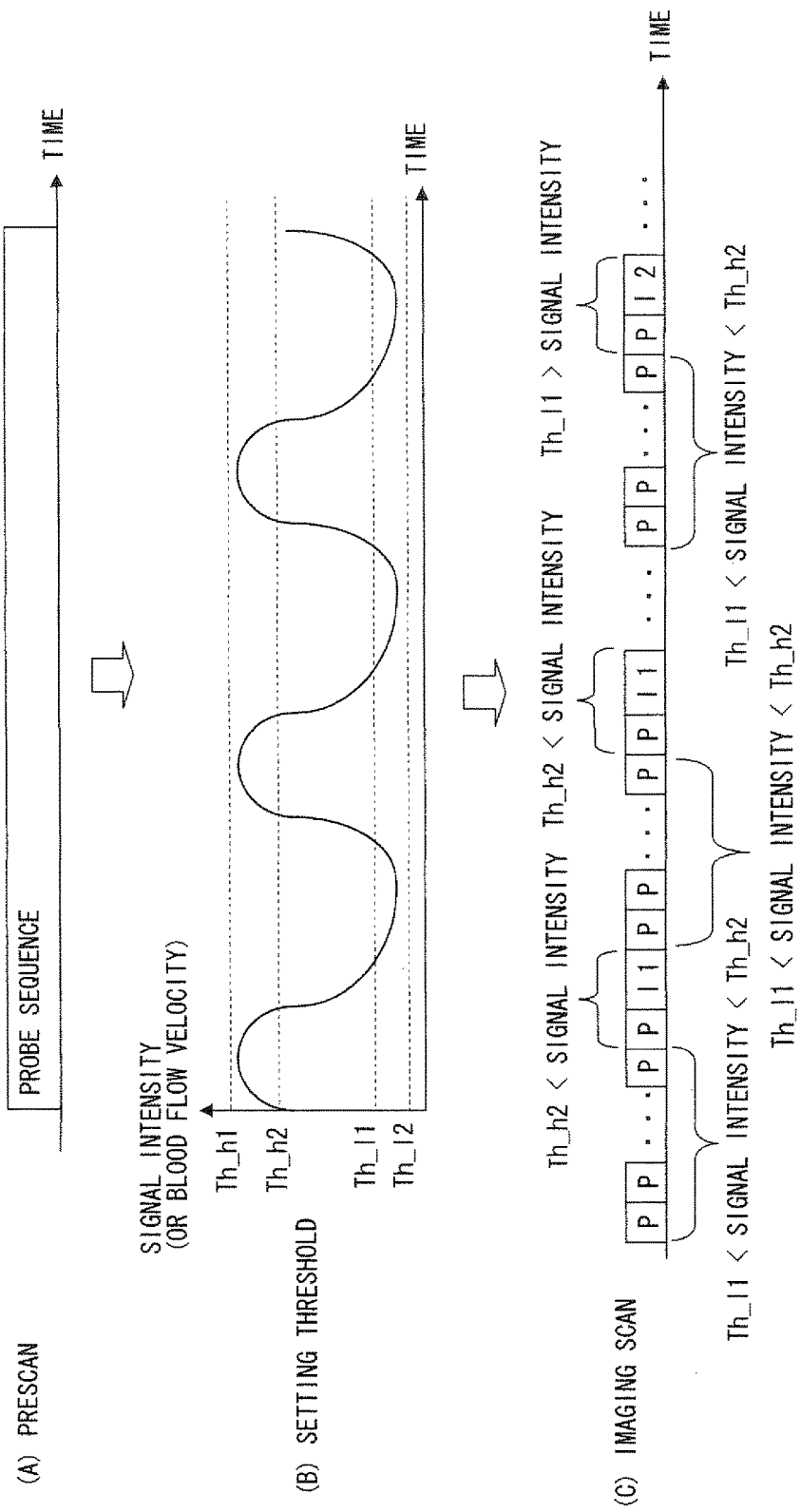
FIG. 9 is a diagram showing another example of procedure for performing a pre-scan and an imaging scan according to a probe sequence and an imaging sequence set in the imaging condition setting unit shown in FIG. 5.

FIG. 9 is a diagram showing another example of procedure for performing a pre-scan and an imaging scan according to a probe sequence and an imaging sequence set in the imaging condition setting unit 40 shown in FIG. 5.

In FIGS. 9, (A), (B) and (C) respectively show a pre-scan with a probe sequence, an example of setting thresholds based on blood flow information acquired by the pre scan and an imaging scan in which an imaging sequence I1 or I2 starts at a timing corresponding to a predetermined signal intensity or velocity of blood flow with repeating the probe sequence P. Each abscissa axis of (A), (B) and (C) in FIG. 9 denotes time, and the ordinate axis of (B) in FIG. 9 denotes intensity of blood flow signal or velocity of blood flow.

Note that, the ordinate axis of FIG. 9 (B) may be a phase change amount of a blood flow signal. When a phase change amount of a blood flow signal is calculated as blood flow information by taking a difference between a signal to be a reference and a signal at each time phase, it is preferable to newly determine a signal to be a reference whenever an imaging sequences I1 or I2 has been completed from the perspective of obtaining the blood flow information as appropriate values. For example, the signal acquired by the first probe sequence P among probe sequences P performed repeatedly can be determined to the signal to be a reference.

When the probe sequences set as shown in FIG. 9 (A) are performed, the probe data shown in FIG. 9 (B) can be obtained. As shown in FIG. 9 (B), not only a threshold Th_h1 on the upper limit side and a threshold Th_h2 on the lower limit side to determine a range near a local maximal value of the probe data but also a threshold Th_l1 on the upper limit side and a threshold Th_l2 on the lower limit side to determine a range near a local minimal value can be set.

Then, as shown in FIG. 9 (C), the imaging scans are performed. Specifically, when a probe sequence P is performed repeatedly and it is determined that an intensity of a signal from a blood flow, a phase change amount of a blood flow signal or a blood flow velocity acquired by performing a certain probe sequence P is between the threshold Th_1 on the upper limit side and the threshold Th_2 on the lower limit side set to the local maximal value of the probe data, the first imaging sequence I1 is performed subsequent to the probe sequence P. On the other hand, when it is determined that an intensity of a signal from a blood flow, a phase change amount of a blood flow signal or a blood flow velocity acquired by performing a certain probe sequence P is between the threshold Tl_1 on the upper limit side and the threshold Tl_2 on the lower limit side set to the local minimal value of the probe data, the second imaging sequence I2 is performed subsequent to the probe sequence P. Then, the probe sequences P is performed repeatedly again subsequent to the first imaging sequence I1 and the second imaging sequence I2. When the control of pulse sequences like this is performed, a single or plural probe sequences P and an imaging sequences I1 or I2 are performed repeatedly alternately as shown in FIG. 9 (C).

If the above-mentioned imaging scan is performed, imaging data can be acquired in appropriate timings while suppressing increase of an imaging time since a period when imaging data is not acquired becomes only a period of all the probe sequences P. Especially, the FBI method is a method to wait for the recovery of the T2 magnetization component in blood and to obtain blood vessel image data having the enhanced T2 magnetization component by performing a three dimensional scan for acquiring echo data (volume data) corresponding to a predetermined slice encode amount. For this reason, under the FBI method, a TR of an imaging sequence becomes long and imaging data is repeatedly acquired every plural heart rates in many cases. Therefore, the imaging scan shown in FIG. 9 is suitable for imaging under the FBI method.

When pieces of imaging data are acquired in a period near a local maximal value and a period near a local minimal value of the probe data, corresponding to a diastole and a systole of a heart respectively, and pieces of imaging data are generated under the FBI method, blood vessel image data in which signals from an artery are enhanced and blood vessel image data in which the signals from the artery are suppressed can be obtained. Therefore, it becomes possible to generate blood vessel image data with arteriovenous separation by subtraction processing of these pieces of blood vessel image data.

Note that, for MRA without using the FBI method, an imaging scan in which a probe sequence is repeated until a signal intensity of a blood flow, a phase change amount of a blood flow signal or a blood flow velocity acquired by a probe sequence becomes within a range defined by thresholds as shown in FIG. 9 may be performed.

Then, other functions of the computer 32 will be described.

The sequence controller control unit 41 has a function for controlling the driving of the sequence controller 31 by giving an imaging condition including a pulse sequence, acquired from the imaging condition setting unit 40, to the sequence controller 31 in response to instruction for starting a scan from the input device 33. The sequence controller control unit 41 also has a function for receiving raw data from the sequence controller 31 and arranging the raw data to k space formed in the k-space database 42. Therefore, the k-space database 42 stores the raw data as k space data.

The image reconstruction unit 43 has a function for reconstructing image data from k-space data by capturing the k-space data from the k-space database 42 and performing image reconstruction processing including FT (Fourier transform) of the k-space data, and writing the generated image data to the image database 44. Therefore, the image database 44 stores the image data.

The blood flow image generating unit 45 has a function for generating angio image data for displaying by performing image processing such as subtraction processing and display processing such as MIP (maximum intensity projection) processing of necessary image data read form the image database 44 and displaying an angio image on the display unit 34 by supplying the generated angio image data with the display unit 34.

Especially, when echo data is acquired by PI, plural pieces of image data corresponding to plural coil elements 24c are to be stored in the image database 44. Therefore, it is necessary to perform unfolding processing, which is post processing in PI, of the plural pieces of image data based on conditions of PI to generate unfolded image data. To this purpose, a function to perform unfolding processing in PI is also provided with the blood flow image generating unit 45. Note that, sensitivity distribution data of each coil element 24c is stored in the blood flow image generating unit 45 since the sensitivity distribution data is used in the unfolding processing.

(Operation and Action)

Then, the operation and action of a magnetic resonance imaging apparatus 20 will be described.

Figure 10:
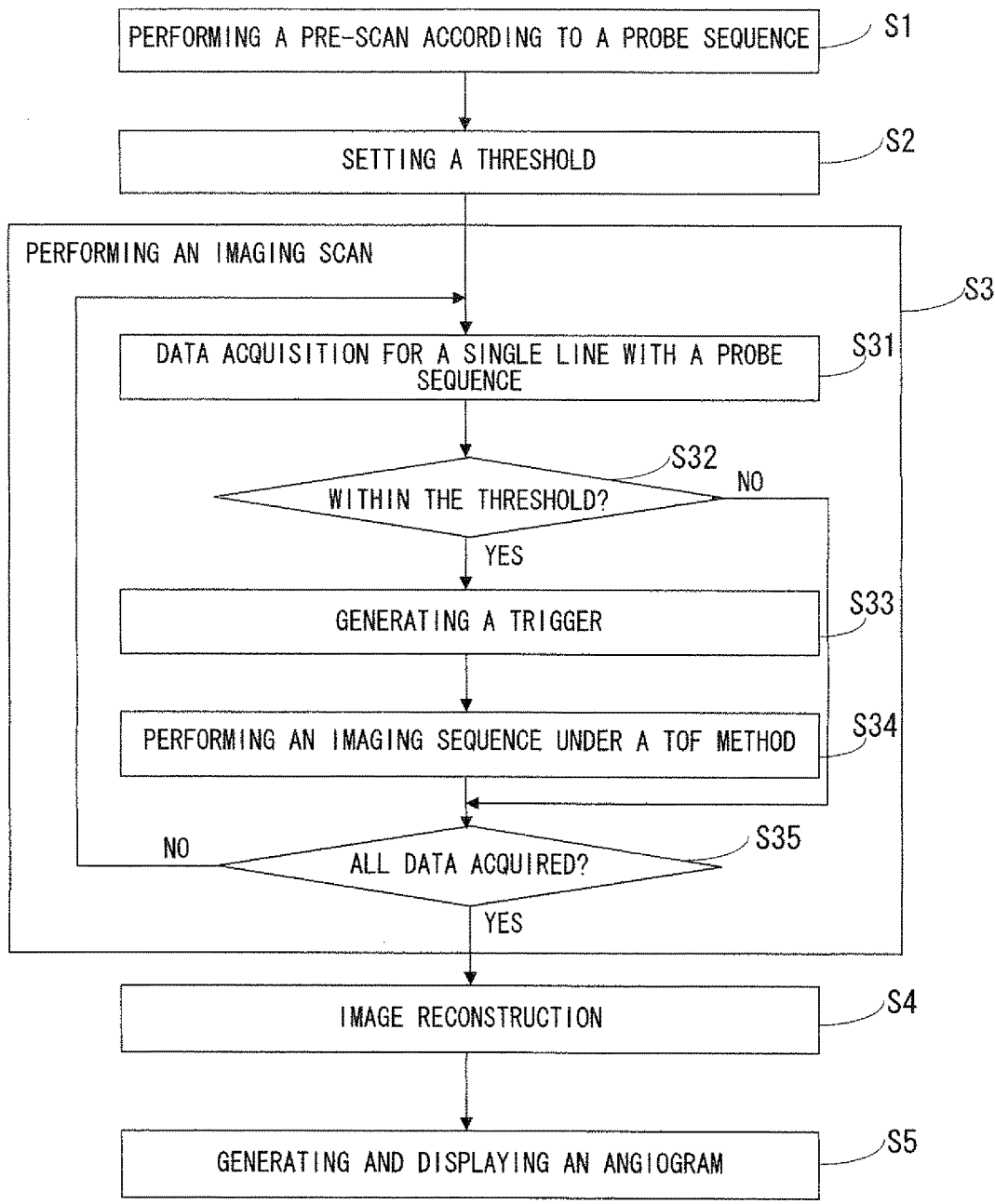
FIG. 10 is a flowchart showing a procedure for acquiring a blood vessel image of an object under a TOF method with the magnetic resonance imaging apparatus shown in FIG. 1.

FIG. 10 is a flowchart showing a procedure for acquiring a blood vessel image of an object P under a TOF method with the magnetic resonance imaging apparatus 20 shown in FIG. 1. The symbols each including S with a number in FIG. 10 indicate respective steps of the flowchart.

First, the object P is set to the bed 37 previously, and a static magnetic field is generated at an imaging area of the magnet 21 (a superconducting magnet) for static magnetic field excited by the static-magnetic-field power supply 26. Further, the shim-coil power supply 28 supplies current to the shim coil 22, thereby uniformizing the static magnetic field generated at the imaging area.

Then, in step S1, an imaging condition for a pre-scan including a probe sequence is set in the imaging condition setting unit 40 and a dynamic probe scan is performed. The probe sequence is set in the probe sequence setting unit 40A. Consequently, probe data showing a time variation of an intensity of a blood flow signal, a phase change amount of a blood flow signal or a blood flow velocity can be obtained. For example, a local region including a lower target blood vessel than that in an imaging region is excited and blood flow signals are acquired from an entire volume. Then, the time variation of the blood flow signals is observed. The detailed flow for acquisition of the probe data, which is described below, is similar to the flow for acquisition of imaging data.

Next, in step S2, thresholds to specify ranges near a local maximal value and/or a local minimal value of the probe data are set automatically or manually by a user in the threshold setting unit 40C.

Next, in step S3, an imaging scan is performed. More specifically, in step S31, the probe sequence set in the probe sequence setting unit 40A is performed and k-space data for a single line is acquired. Then, the acquired k-space data is stored in the k-space database 42.

Next, the trigger setting unit 40D obtains k-space data from the k-space database 42 and calculates an intensity of a blood flow signal. Subsequently, in step S32, the trigger setting unit 40D determines whether the intensity of the blood flow signal is within the range specified by the thresholds or not. Then, when the intensity of the blood flow signal is determined to be within the range specified by the thresholds, the trigger setting unit 40D generates a trigger signal in step S33.

Then, in step S34, an imaging sequence for acquiring imaging data is performed under a TOF method. For example, the imaging data is acquired under a segment k-space method which divides the k-space into several regions to make segments and captures k-space data for each segment sequentially.

Specifically, the imaging sequence is supplied from the imaging condition setting unit 40 to the sequence controller control unit 41 in response to generation of a trigger signal. Then, the sequence controller control unit 41 supplies the imaging sequence to the sequence controller 31. Therefore, the sequence controller 31 drives the gradient power supply 27, the transmitter 29, and the receiver 30 in accordance with the imaging sequence received from the sequence controller control unit 41, thereby generating a gradient magnetic field at an imaging area having the set object P, and further generating RF signals from the RF coil 24.

Consequently, the RF coil 24 receives NMR signals generated due to nuclear magnetic resonance in the object P. Then, the receiver 30 receives the NMR signals from the RF coil 24 and generates raw data. The receiver 30 supplies the generated raw data to the sequence controller 31. The sequence controller 31 supplies the raw data to the sequence controller control unit 41. The sequence controller control unit 41 arranges the raw data to the k space formed in the k-space database 42.

As mentioned above, the imaging data in the corresponding segment is acquired. When acquisition of the pieces of imaging data corresponding to all segments has been completed, it is determined YES in step S35. On the other hand, when acquisition of the pieces of imaging data corresponding to all segments has not been completed, it is determined NO in step S35 and acquisition of the imaging data for the following segment is performed again according to the procedure from step S31 repeatedly until it is determined YES.

In step S32, when the intensity of the blood flow signal is determined not to be within the range specified by the thresholds, the determination of step S35 is performed without performing generation of a trigger and acquisition of imaging data.

When it is determined to be YES in step S35, the image reconstruction unit 43 reads the k-space data from the k-space database 42 and performs image reconstruction processing of the read k-space data, thereby generating image data in step S4. The generated image data is stored in the image database 44.

Subsequently, in step S5, the blood flow image processing unit 45 reads the image data form the image database 44 and generates blood vessel image data for display. Then, the generated blood vessel image data is displayed on the display unit 34. Note that, unfolding processing is performed on plural pieces of image data corresponding to plural coil elements 24c in case of performing PI.

Since the angiogram displayed on the display unit 34 in this way is generated from the imaging data acquired at timing at which an intensity of a blood flow signal becomes close to a local maximal value, it becomes an image depicting a blood vessel satisfactorily. Therefore, a useful angiogram for a diagnosis can be obtained.

Next, an example of angio imaging by a SSFP sequence will be described.

Figure 11:
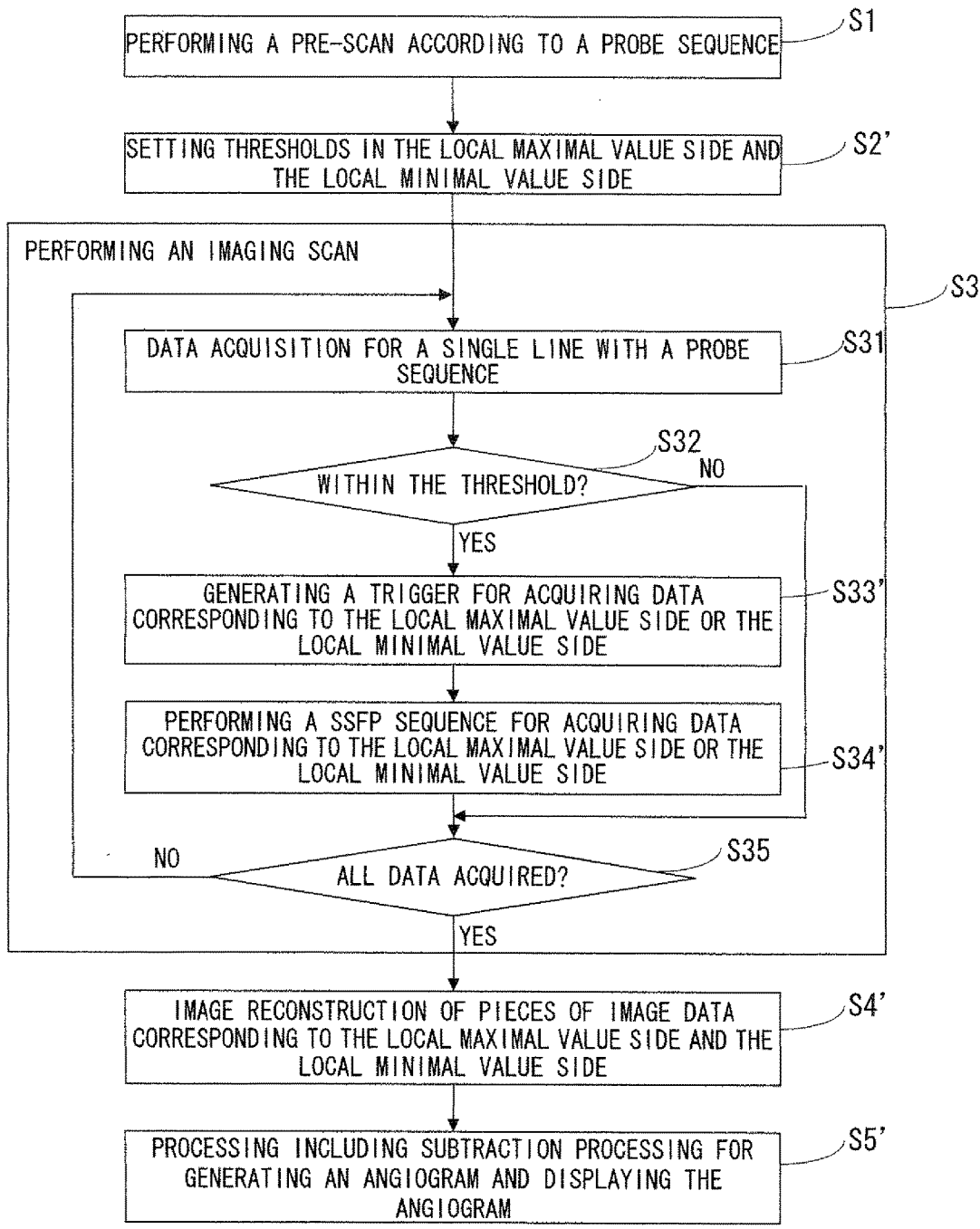
FIG. 11 is a flowchart showing a procedure for acquiring a blood vessel image of an object with subtraction processing by using a SSFP sequence as an imaging sequence with the magnetic resonance imaging apparatus shown in FIG. 1.

FIG. 11 is a flowchart showing a procedure for acquiring a blood vessel image of an object P with subtraction processing by using a SSFP sequence as an imaging sequence with the magnetic resonance imaging apparatus 20 shown in FIG. 1. The symbols each including S with a number in FIG.

11 indicate respective steps of the flowchart. Note that, explanation of steps equivalent to those shown in FIG. 10 is omitted with attaching same numbers.

In the case of performing subtraction processing between image data acquired at timing at which a blood flow signal becomes a local maximal value and image data acquired at timing at which a blood flow signal becomes a local minimal value for generating an angiogram, thresholds are set in the local maximal value side and the local minimal value side of the probe data respectively in step S2'.

Then, in the threshold determination in step S32, when an intensity of a blood flow signal is determined to be within the range specified by the thresholds in the local maximal value side, a trigger for starting a SSFP sequence for acquiring imaging data is generated for a period when the blood flow signal reaches the local maximal value in step S33'. On the other hand, in the threshold determination in step S32, when an intensity of a blood flow signal is determined to be within the range specified by the thresholds in the local minimal value side, a trigger for starting a SSFP sequence for acquiring imaging data is generated for a period when the blood flow signal reaches the local minimal value in step S33'.

Next, in step S34', the SSFP sequence for acquiring the imaging data is performed for the period when the intensity of the blood flow signal becomes the local maximal value side or the period when the intensity of the blood flow signal becomes the local minimal value side according to the trigger.

When all pieces of data have been acquired, in step S4', the first image data is reconstructed from the pieces of imaging data acquired for the periods when the intensities of the blood flow signals become the local maximal value side and the second image data is reconstructed from the pieces of imaging data acquired for the periods when the intensities of the blood flow signals become the local minimal value side.

Next, In step S5', blood vessel image data generation processing including subtraction processing between the first image data and the second image data is performed in the blood flow image generating unit 45. Then, the generated blood vessel data is displayed on the display unit 34.

The angiogram displayed on the display unit 34 as mentioned above is generated by subtraction processing between the image data depicting the blood vessel based on the imaging data acquired for the periods when the intensities of the blood flow signals become the local maximal values and the image data having the suppressed blood vessel based on the imaging data acquired for the periods when the intensities of the blood flow signals become the local minimal values. For this reason, the angiogram becomes an image in which the target blood vessel is enhanced satisfactorily. Consequently, a useful angiogram for a diagnosis can be obtained.

Next, an example of angio imaging under a FBI method will be described.

Figure 12:
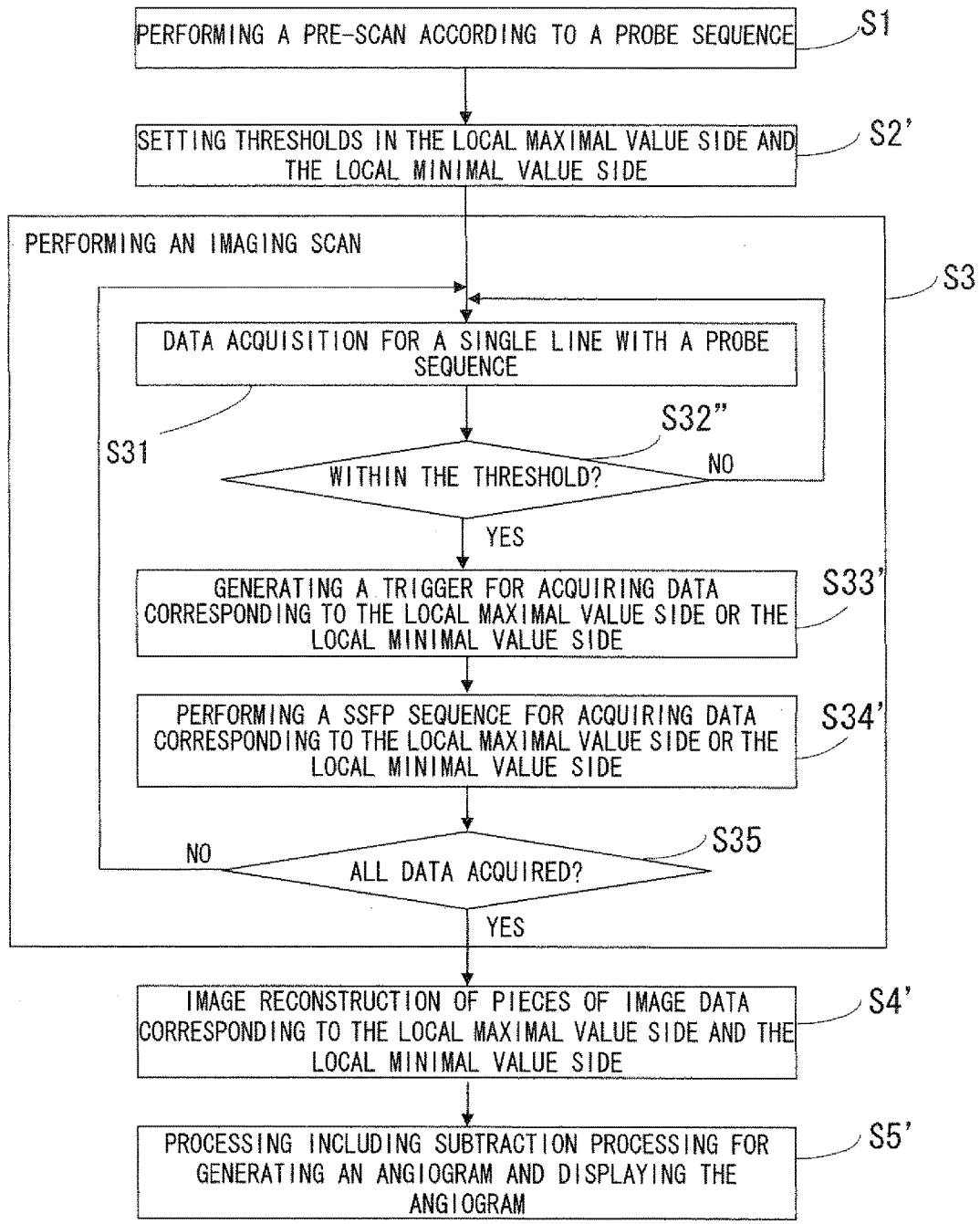
FIG. 12 is a flowchart showing a procedure for acquiring a blood vessel image of an object with subtraction processing under a FBI method with the magnetic resonance imaging apparatus shown in FIG. 1.

FIG. 12 is a flowchart showing a procedure for acquiring a blood vessel image of an object P with subtraction processing under a FBI method with the magnetic resonance imaging apparatus 20 shown in FIG. 1. The symbols each including S with a number in FIG. 12 indicate respective steps of the flowchart. Note that, explanation of steps equivalent to those shown in FIG. 11 is omitted with attaching same numbers.

In the case of imaging under an FBI method, a TR of an imaging sequence becomes equivalent to one period or more of probe data. For that reason, as shown in step S32", when an intensity of a blood flow signal acquired with a probe sequence in an imaging scan is not within a range defined by thresholds, data acquisition for a single line with a probe sequence is performed again in step S31.

Thus, in step S32", only when it is determined that an intensity of a blood flow signal acquired with a probe sequence is within the range defined by the thresholds, imaging data is acquired with a sequence such as a FSE sequence or a FASE sequence according to the procedure from step 33'.

Therefore, constantly, it is possible to acquire imaging data in an appropriate timing based on an intensity of a blood flow signal. Consequently, an angiogram in which a target blood vessel is enhanced satisfactorily can be generated.

That is, the magnetic resonance imaging apparatus 20 as mentioned above is an apparatus to acquire data for imaging with triggers generated based on blood flow information such as an intensity of a blood flow signal, a phase change amount of a blood flow signal or a blood flow velocity from a blood vessel to be a target. More specifically, the magnetic resonance imaging apparatus 20 is an apparatus which acquires imaging data when a signal intensity of blood flow, a phase change amount of a blood flow signal or a blood flow velocity obtained in an imaging scan becomes within a predetermined range specified by thresholds set in advance.

(Effect)

Therefore, according to the magnetic resonance imaging apparatus 20, it becomes possible to acquire imaging data at appropriate timings depending on the blood flow information obtained in real time. This allows a depicting performance in an angiogram to be improved. This effect becomes remarkable especially when a non-contrast-enhanced MRA in which acquisition timings of imaging data are significant is performed.

That is, an pre-scan such as an ECG-prep scan is performed and acquisition of imaging data is performed at an acquisition timing (a delay time) which was thought to be appropriate when the pre-scan was performed conventionally. Therefore, an appropriate acquisition timing (delay time) of the imaging data may change in case where a state of a blood flow changes between timings at which the pre-scan is performed and an imaging scan is performed.

To the contrary, since the magnetic resonance imaging apparatus 20 generates a trigger used for starting an imaging sequence based on blood flow information of a blood vessel to be a target observed intermittently or continuously during an imaging scan. Therefore, imaging data can be acquired at more satisfactory timing adapting to a state of an object P during the imaging scan. For this reason, that is expected as a technology that replaces the pre-scan method used conventionally. Then, it becomes possible to generate a stable angiogram by performing data acquisition constantly at satisfactory timings.

Additionally, a trigger can be generated at an arbitrary timing based on blood flow information. Consequently, an image can be obtained with a stable contrast by generating triggers so that each piece of imaging data is acquired at a timing at which an intensity of a blood flow signal is low or a timing at which a blood flow velocity is slow even in case of acquiring a black blood image of which brightness is suppressed in a blood vessel part.

In addition, since a pre-scan for acquiring probe data needs a short time as compared with a pre-scan such as an ECG-prep scan performed over plural heart rates with changing a delay time, an imaging time can be shortened.

Moreover, according to the magnetic resonance imaging apparatus 20, an ECG synchronous is unnecessary and not only an FBI method but also a various imaging method such as a TOF method can be adapted. That is, the ECG synchronous can be made useless in the FBI method.

What is claimed is:

1. A magnetic resonance imaging (MRI) apparatus comprising:
   static and gradient magnetic field generators, at least one radio frequency (RF) coil configured to be coupled to an imaging volume, RF transmitter and receiver circuits coupled to the RF coil and at least one programmable computer connected to control said gradient magnetic field generator, said RF transmitter and receiver circuits, the at least one programmable computer being configured to
   provide a probe sequence and acquire blood flow information of an object within an imaging scan to acquire magnetic resonance signals from the object and to generate a trigger for an imaging sequence, also within said imaging scan, using the blood flow information acquired in the probe sequence, wherein a data acquisition region of the probe sequence is set to a local region including at least a target blood vessel, and the blood flow information is acquired from magnetic resonance signals obtained from the target blood vessel;
   acquire imaging data from the object during said imaging sequence initiated by the trigger and to generate blood flow image data using the acquired imaging data; and
   repeatedly and alternately perform, during said imaging scan, (a) said probe sequence acquiring the blood flow information and (b) the imaging sequence acquiring the imaging data,
   wherein the local region to which the probe sequence is applied is located downstream of a region to which the imaging sequence is applied.

2. The magnetic resonance imaging apparatus of claim 1, wherein the at least one programmable computer being further configured to acquire
   a signal from blood flow in a target blood vessel, and an absolute value of intensity of the signal or a luminance value of image data generated from the signal as the blood flow information.

3. The magnetic resonance imaging apparatus of claim 1, wherein the at least one programmable computer being further configured to acquire
   a velocity of blood flow in a target blood vessel as the blood flow information.

4. The magnetic resonance imaging apparatus of claim 1, wherein the at least one programmable computer being further configured to acquire a temporal phase shift amount of a signal from blood flow in a target blood vessel as the blood flow information.

5. The magnetic resonance imaging apparatus of claim 4, wherein the at least one programmable computer being further configured to acquire
   a difference in phase between a signal corresponding to each time phase and a reference signal as the temporal phase shift amount.

6. The magnetic resonance imaging apparatus of claim 4, wherein the at least one programmable computer being further configured to acquire
   a difference in phase between signals adjacent to each other in time as the temporal phase shift amount.

7. The magnetic resonance imaging apparatus of claim 1, wherein the at least one programmable computer being further configured to acquire the blood flow information by NMR RF (nuclear magnetic resonance radio frequency) excitation of a local region including a target blood vessel at a downstream side of a region for acquiring the imaging data.

8. The magnetic resonance imaging apparatus of claim 1, wherein the at least one programmable computer being further configured to acquire
   a velocity of blood flow in a target blood vessel as the blood flow information by NMR RF (nuclear magnetic resonance radio frequency) excitation of a local region including the target blood vessel with a sequence using a phase contrast MRI method.

9. The magnetic resonance imaging apparatus of claim 1, wherein the at least one programmable computer being further configured to generate
   the trigger when it is determined that the blood flow information is within a range specified by preset thresholds.

10. A magnetic resonance imaging apparatus of claim 1, wherein the at least one programmable computer being further configured to acquire
    k-space data corresponding to one line passing through a center of k-space by NMR RF (nuclear magnetic resonance radio frequency) excitation of a local region including a target blood vessel with a sequence of a field echo or a spin echo type and to generate the trigger is generated when it is determined that the blood flow information is within a range specified by preset thresholds, the threshold values being obtained from the k-space data.

11. The magnetic resonance imaging apparatus of claim 1, wherein the at least one programmable computer being further configured to
    (a) generate a trigger for a first imaging sequence to be performed in a period when the blood flow information is within a local maximal range specified by preset thresholds and (b) generate a trigger for a second imaging sequence to be performed in a period when the blood flow information is within a local minimal range specified by further preset thresholds, and
    generate the blood flow image data by subtraction processing between first imaging data acquired by the first imaging sequence and second imaging data acquired by the second imaging sequence.

12. The magnetic resonance imaging apparatus of claim 1, wherein the at least one programmable computer being further configured to acquire
    the magnetic resonance signals repeatedly at a predetermined interval and the trigger is generated only when it is determined that the blood flow information is within a range specified by preset thresholds obtained from the magnetic resonance signals.

13. The magnetic resonance imaging apparatus of claim 1, wherein the at least one programmable computer being further configured to acquire
    the magnetic resonance signals repeatedly until it is determined that the blood flow information is within a range specified by preset thresholds and the trigger is generated when it is determined that the blood flow information is within the range based on the magnetic resonance signals.

14. The magnetic resonance imaging apparatus of claim 1, wherein the at least one programmable computer being further configured to generate the blood flow image data as T2 weighted image data by acquiring the imaging data with a non-contrast-enhanced three dimensional MRI scan using a spin echo type imaging sequence.

15. The magnetic resonance imaging apparatus of claim 1, wherein the at least one programmable computer being further configured to acquire the imaging data using a steady state free precession MRI sequence.

16. The magnetic resonance imaging apparatus of claim 1, wherein the at least one programmable computer being further configured to acquire saturated blood signals flowing into an imaging section as the imaging data using a field echo type MRI sequence wherein a saturation pulse is applied to a target blood flow and using an inflow effect of a time of flight method without using contrast medium.

17. A magnetic resonance imaging (MRI) method comprising: operating an MRI system including static and gradient magnetic field generators, at least one radio frequency (RF) coil configured to be coupled to an imaging volume, RF transmitter and receiver circuits coupled to the RF coil and at least one programmed computer to (a) acquire blood flow information of an object by acquiring magnetic resonance signals from the object and generating a trigger, for an imaging sequence during an imaging scan that includes both the probe sequence and the imaging sequence, using the blood flow information acquired in the probe sequence, wherein a data acquisition region of the probe sequence is set to a local region including at least a target blood vessel, and the blood flow information is acquired from magnetic resonance signals obtained from the target blood vessel;

(b) acquire imaging data from the object during said imaging sequence initiated by the trigger and generate blood flow image data using the acquired imaging data; and (c) repeatedly and alternately perform, during said imaging scan, (a) the probe sequence acquiring the blood flow information and (b) the imaging sequence acquiring the imaging data, wherein the local region to which the probe sequence is applied is located downstream of a region to which the imaging sequence is applied.

\* \* \* \* \*